United States Patent
Cheekoori

(10) Patent No.: US 11,903,920 B2
(45) Date of Patent: Feb. 20, 2024

(54) CANNABINOID FORMULATION: PRODUCTION METHOD AND USE

(71) Applicant: CHIROSYN DISCOVERY TECHNOLOGIES INC., Toronto (CA)

(72) Inventor: Sreedhar Cheekoori, Toronto (CA)

(73) Assignee: CHIROSYN DISCOVERY TECHNOLOGIES INC., Toronto (CA)

( * ) Notice: Subject to any disclaimer, the term of this patent is extended or adjusted under 35 U.S.C. 154(b) by 0 days.

(21) Appl. No.: 17/649,938

(22) Filed: Feb. 4, 2022

(65) Prior Publication Data

US 2023/0248690 A1    Aug. 10, 2023

(51) Int. Cl.
| | |
|---|---|
| *A61K 31/352* | (2006.01) |
| *A61K 31/05* | (2006.01) |
| *A61K 45/06* | (2006.01) |
| *A61K 9/16* | (2006.01) |
| *A61K 9/107* | (2006.01) |
| *A61K 47/44* | (2017.01) |

(52) U.S. Cl.
CPC ............ *A61K 31/352* (2013.01); *A61K 9/107* (2013.01); *A61K 9/1611* (2013.01); *A61K 31/05* (2013.01); *A61K 45/06* (2013.01); *A61K 47/44* (2013.01)

(58) Field of Classification Search
CPC .... A61K 31/352; A61K 9/107; A61K 9/1611; A61K 31/05; A61K 45/06; A61K 47/44
See application file for complete search history.

(56) References Cited

U.S. PATENT DOCUMENTS

| | | | |
|---|---|---|---|
| 9,572,834 B2 * | 2/2017 | Tour ........................ | A61K 33/44 |
| 2010/0129457 A1 * | 5/2010 | Razavi ............... | A61K 47/6929 |
| | | | 977/773 |

FOREIGN PATENT DOCUMENTS

| | | | | |
|---|---|---|---|---|
| CA | 3050473 A1 * | 2/2020 | ............... | A23L 2/54 |
| CN | 113499324 | 8/2022 | | |
| WO | WO-2021123804 A1 * | 6/2021 | ............. | A61K 31/05 |

OTHER PUBLICATIONS

Trucillo P. Drug Carriers: Classification, Administration, Release Profiles, and Industrial Approach. Processes. 2021; 9(3):470. https://doi.org/10.3390/pr9030470 (Year: 2021).*
Nakano et al., "Development of a Novel Nanoemulsion Formulation to Improve Intestinal Absorption of Cannabidiol"; Med. Cannabis Cannabinoids (2019) 2:35-42.
World Health Organization Expert Committee on Drug Dependence: Cannabidiol (CBD) Pre-Review Report Agenda Item 5.2 and Peer Review, 39th ECDD (2017) Agenda Item 5.2.
Atsmon et al., "Single-Dose Pharmacokinetics of Oral Cannabidiol Following Administration of PTL101: A New Formulation Based on Gelatin Matrix Pellets Technology"; Clinical Pharmacology in Drug Development Sep. 2018;7(7):751-758.
Larsena et al., "Dosage, Efficacy and Safety of Cannabidiol Administration in Adults: A Systematic Review of Human Trials"; J. Clin. Med. Res. (2020) 12(3):129-141.
Thomas et al., "Cannabidiol displays unexpectedly high potency as an antagonist of CB1 and CB2 receptor agonists in vitro"; Br. J. Pharmacol. (2007) 150(5):613-23.
Welty et al., "Cannabidiol: Promise and Pitfalls, Epilepsy Currents"; (2014) 14(5): 250-252.
Knaub et al., "A Novel Self-Emulsifying Drug Delivery System (SEDDS) Based on VESIsorbfi Formulation Technology Improving the Oral Bioavailability of Cannabidiol in Healthy Subjects"; Molecules (2019) 24, 2967.
Millar et al., "Towards Better Delivery of Cannabidiol (CBD)"; Pharmaceuticals (2020) 13, 219.
Office Action dated Mar. 2, 2023 by the Canadian Intellectual Property Office in the corresponding Canadian Application No. 3, 147,817.
Zi Chen, "Revolution in Biomedicine: A Leap Forward on the Eventual Fate of Clinical Diagnosis and Treatment", Journal of Biomedical Systems & Emerging Technologies, vol. 9, No. 4 Mini Review, 2022.

* cited by examiner

*Primary Examiner* — Brandon J Fetterolf
*Assistant Examiner* — Manahil Mirghani Ali Abdalhameed
(74) *Attorney, Agent, or Firm* — LAVERY, DE BILLY, LLP; Béatrice Ngatcha

(57) ABSTRACT

An oil-based formulation comprising a cannabinoid and pico size carbon particles. The formulation is suitable for administration to a patient having a medical condition requiring the use of cannabinoid.

15 Claims, 2 Drawing Sheets

CANNABINOID FORMULATION: PRODUCTION METHOD AND USE

FIELD OF THE INVENTION

The present invention relates generally to formulations comprising a cannabinoid. More specifically, the invention relates to an oil-based formulation comprising a cannabinoid and pico size carbon particles. The cannabinoid in the formulation may be cannabidiol (CBD).

BACKGROUND OF THE INVENTION

*Cannabis sativa* L. is one of the oldest known medicinal plants and has been extensively studied with respect to its phytochemistry. A cannabis plant extract comprises around 483 identified compounds belonging to various chemical classes. Of these classes, the cannabinoid class comprises unique compounds, known to exist only in *Cannabis sativa* L. There are 66 known plant-derived cannabinoid compounds, the most prevalent of which are Δ-9-tetrahydrocannabinol (THC or Δ-9THC or dronabinol), cannabidiol (CBD) and cannabinol (CBN). Other cannabinoids include cannabigerol (CBG), cannabichromene (CBC) and cannabinodiols (CBND). Cannabidiol (CBD) and Δ-9-tetrahydrocannabinol (THC) are the most researched/studied cannabinoids.

Δ-tetrahydrocannabinol (THC) has the systematic name (-)-(6aR,10aR)-6,6,9-trimethyl-3-pentyl-6a,7,8,10a-tetrahydro-6H-benzo[c]chromen-1-ol, is a naturally occurring compound and is the primary active ingredient in the controlled substance marijuana. The pharmacological activity of THC is due to its binding to the type 1 cannabinoid protein receptor (CB1) and activation, thus generating biological effects including analgesia, muscle relaxation, anti-emesis, and appetite stimulation. Currently, THC is commercially available in the U.S. as an orally administered soft gelatin capsule under the trade name Marinol® and is indicated for the treatment of anorexia associated with weight loss in patients with AIDS, as well as nausea and vomiting associated with cancer chemotherapy in patients who have failed to respond adequately to conventional antiemetic treatments.

Cannabidiol (CBD) has the systematic name 2-[1R-3-methyl-6R-(1-methylethenyl)-2-cyclohexen-1-yl]-5-pentyl-1,3-benzenediol or 2-[(6R)-3-methyl-6-prop-1-en-2-ylcyclohex-2-en-1-yl]-5-pentylbenzene-1,3-diol. CBD is a non-psychoactive cannabinoid which preferentially binds to the type 2 cannabinoid receptor (CB2) and has been shown to have analgesic, anticonvulsive, antiemetic, anxiolytic, antioxidant, anti-psychotic properties, as well as utility as a muscle relaxant. CBD has a melting point of 62-63° C. and solubility of approximately 23.6 mg/mL in DSMO and ethanol.

CBD has been demonstrated as an effective treatment of epilepsy in several clinical trials. In this regard, a product comprising pure CBD (Epidiolex®) was recently approved by the United States Food and Drug Administration (FDA). There are many un-approved (also not proven) medical uses of CBD-based products in forms such as oils, supplements, gums, as well as high concentration extracts available online for the treatment of various ailments.

It is known in the art that effects generated by CBD are different from those generated by THC. Indeed, the two compounds bind to different types of cannabinoid receptor as outlined above. THC has been shown to generate most of the effects which occur when CB1 is activated including suppression of locomotor activity, hypothermia and antinociception. On the other hand, it has been shown that CBD generates effects on the heart rate or blood pressure under normal conditions. However, in animal models of stress, CBD reduces the heart rate and blood pressure.

Typically, cannabis-derived medicinal analgesics have been used to treat a variety of disorders including gout, rheumatism, malaria, pain, and fever. CBD is one of the major non-psychoactive components present *Cannabis sativa* L. extract [1]. Cannabidiol, a 21-carbon terpenophenolic, is generally obtained by decarboxylation of a cannabidiol acid precursor [2].

The endocannabinoid system (ECS) comprises cannabinoid receptors type 1 (CB1) and type 2 (CB2) as indicated above. These receptors are distributed throughout the nervous system, immune cells, and lipid-based retrograde neurotransmitters as ligands [3,4]. Exogenous cannabinoids exploit this system to exert pain modulation and psychoactive effects. Although Δ9-tetrahydrocannbinol (THC) shows higher binding affinity towards CB1 compared to CBD, non-psychoactive properties depict CBD as an exclusive therapeutic agent. But CBD have also been reported to show unexpectedly higher antagonism than cannabidiol agonists [5]. Studies have shown that cannabidiol is a promising therapeutic agent as antioxidant, anti-inflammatory, analgesic, antitumor, neuroprotectant having anti-anxiety activities [1,3].

The half-life of CBD varies from 1.4 hours to 5 days depending on the method and route of administration. Typically, the half-time of CBD is between 2 to 5 days when administered orally. Several research groups have undertaken research projects aimed at improving the bioavailability of CBD including enhancing its intestinal absorption and solubility [6,7,1,8].

There is still a need for formulations containing a cannabinoid, particularly CBD. There is a need for such formulations which allow for an improved bioavailability of the cannabinoid.

SUMMARY OF THE INVENTION

The inventors have designed and prepared an oil-based formulation comprising a cannabinoid and pico size carbon particles. In embodiments of the invention, the cannabinoid is cannabidiol (CBD).

In embodiments of the invention, the CBD is provided in a first oil-based material, and the pico size carbon particles are suspended in a second oil-based material. The first oil-based material and the second oil-based material may be the same or different.

In embodiments of the invention, the first oil-based material is sesame oil or any other suitable oil, and the second oil-based material is tall oil or any other suitable oil.

The invention thus provides the following in accordance with aspects thereof:
(1) An oil-based formulation comprising a cannabinoid and pico size carbon particles.
(2) An oil-based formulation comprising a mixture of a cannabinoid dissolved in a first oil-based material and pico size carbon particles suspended in a second oil-based material.
(3) The oil-based formulation according to (1) or (2), wherein the cannabinoid is purified from a cannabis extract or the cannabinoid is synthesized.
(4) The oil-based formulation according to (1) or (2), wherein the cannabinoid is a cannabis extract enriched in cannabidiol (CBD).

(5) The oil-based formulation according to any one of (1) to (4), wherein the cannabinoid comprises cannabidiol (CBD) and one or more of: tetrahydrocannabinol (Δ9-THC), cannabichromene (CBC), cannabigerol (CBG), cannabinol (CBN), cannabidivarol (CBDV), and a salt of the cannabinoid.

(6) The oil-based formulation according to any one of (1) to (5), wherein the cannabinoid is cannabidiol (CBD).

(7) The oil-based formulation according to (2), wherein the first and second oil-based materials are each independently selected from the group consisting of: sesame oil, tall oil, hydrocarbon, higher fatty acid, higher alcohol, fatty acid ester of polyhydric alcohol, higher alcohol ether of polyhydric alcohol, polymer or copolymer of alkylene oxide, long chain triglycerides (LCT), medium chain triglycerides (MCT), and a combination thereof.

(8) The oil-based formulation according to (2), wherein the first oil-based material is sesame oil, and the second oil-based material is tall oil.

(9) An oil-based formulation comprising a mixture of cannabidiol (CBD) dissolved in sesame oil and pico size carbon particles suspended in tall oil.

(10) The oil-based formulation according to any one of (1) to (9), further comprising one or more of: a flavor agent which is artificial or from a natural source, a coloring agent which is artificial or from a natural source, caffeine, an antioxidant, a vitamin, a probiotic, and a mineral.

(11) The oil-based formulation according to any one of (1) to (10), which is suitable for medical administration to a patient in need of cannabinoid.

(12) A method of treating a patient in need of a cannabinoid, comprising administering to the patient a suitable amount of the oil-based formulation as defined in any one of (1) to (10).

(13) Use of the oil-based formulation as defined in any one of (1) to (10), for treating a patient in need of a cannabinoid.

(14) Use of the oil-based formulation as defined in any one of (1) to (10), in the manufacture of a medicament for treating a patient in need of a cannabinoid.

(15) A pharmaceutical composition comprising the oil-based formulation as defined in any one of (1) to (10), and a pharmaceutically acceptable carrier or excipient.

(16) A method for producing a formulation comprising a cannabinoid, the method comprising:
  (a) dissolving a cannabinoid in a first oil-based material to obtain a first mixture;
  (b) providing a suspension of pico size carbon particles in a second oil-based material; and
  (c) adding the suspension to the first mixture and stirring the resulting mixture for a period of time to obtain the formulation.

(17) A method for producing a formulation comprising cannabidiol (CBD), the method comprising:
  (a) dissolving CBD in a sesame oil to obtain a first mixture;
  (b) providing a suspension of pico size carbon particles in tall oil; and
  (c) adding the suspension to the first mixture and stirring the resulting mixture for a period of time to obtain the formulation.

(18) A kit comprising:
  a cannabinoid;
  an oil-based material;
  a suspension of pico size carbon particles in a second oil-based material; and
  instructions for use,
optionally, the use is for the preparation of a medicament for treating a patient in need of a cannabinoid.

(19) A kit comprising:
  cannabidiol (CBD);
  sesame oil;
  a suspension of pico size carbon particles in tall oil; and
  instructions for use,
optionally, the use is for the preparation of a medicament for treating a patient in need of a cannabinoid.

(20) The oil-based formulation according to (11) or the method according to (12) or the use according to (13) or (14) or the kit according to (18) or (19), wherein the patient has a medical condition which is epilepsy; optionally the medical condition is childhood-onset epilepsy selected from Lennox-Gastaut syndrome and Dravet syndrome; optionally administration to the patient is an oral administration; optionally seizure frequency in the patient is reduced; optionally the medical condition is resistant from other treatments including a treatment involving clobazam.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
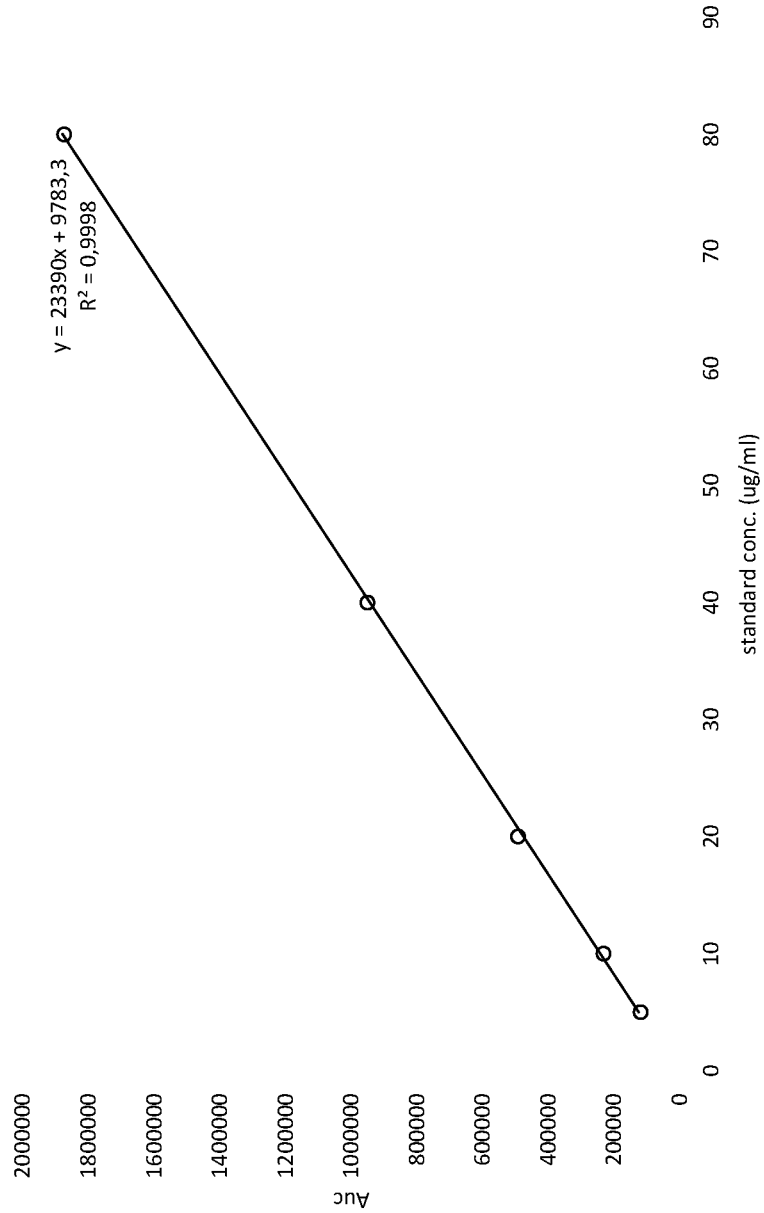
FIG. 1: Calibration curve of cannabidiol (CBD).

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments; and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

Use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein when referring to numerical values or percentages, the term "about" includes variations due to the methods used to determine the values or percentages, statistical variance and human error. Moreover, each numerical parameter in this application should at least be construed in light of the number of reported significant digits and by applying ordinary rounding techniques.

As used herein, the term "pico size carbon particles" refers to carbon particles having an average size of about $1 \times 10^{-12}$ m.

The inventors have designed and an oil-based formulation comprising a cannabinoid and pico size carbon particles. In embodiments of the invention, the cannabinoid is cannabidiol (CBD).

In embodiments of the invention, the CBD is provided in a first oil-based material, and the pico size carbon particles are suspended in a second oil-based material. The first oil-based material and the second oil-based material may be the same or different. In embodiments of the invention, the first oil-based material is sesame oil or any other suitable oil, and the second oil-based material is tall oil or any other suitable oil.

In embodiments of the invention, an oil-based formulation comprising CBD and pico size carbon particles is provided.

In embodiments of the invention, a pharmaceutical composition comprising the CBD formulation according to the invention is provided. The pharmaceutical composition may further comprise a pharmaceutically acceptable carrier or excipient. In embodiments of the invention, the formulation is used in the preparation of a medicament for treating a patient in need of a cannabinoid. Also, the invention relates to a method of treating a patient in need of a cannabinoid, the method comprising using the formulation, or the pharmaceutical composition, or the medicament according to the invention.

In embodiments of the invention, a kit is provided which may be used in the preparation of the CBD formulation, or the pharmaceutical composition, or the medicament according to the invention. The kit may comprise the cannabinoid, an oil-based material for dissolving the cannabinoid, a suspension of pico size carbon material in an oil-based material, and instructions for use to produce the formulation.

In embodiments of the invention, a method for producing the CBD formulation according to the invention is provided. The method comprises providing CBD and dissolving it into an oil-based material. Also, the method comprises providing a suspension of pico size carbon particles in an oil-based material. The suspension is then added to the CBD mixture and the resulting mixture is subjected to stirring for a period of time.

Materials: Cannabidiol powder was obtained from Keminntek Laboratories (Hyderabad, India). Acetonitrile and methanol were the solvents used which are obtained from Fischer scientific pvt. Ltd. (Mumbai, India). The solvent n-hexane was obtained from Finar chemicals (India). The oil-based material consisting of pico size carbon particles suspended in tall oil was obtained from Chirosyn Discovery. Sesame oil was of AS Brand. Oral gavage was obtained from B.I.K. Industries (Mumbai, India).

Example 1—Preparation of samples of Cannabidiol: Two formulations of Cannabidiol (CBD) were analyzed in this study. For the first formulation, 100 mg of CBD powder was dissolved with 1 ml of sesame oil and allowed for overnight mixing. For the second formulation, 100 mg of CBD powder was dissolved with 1 ml of sesame oil followed by the addition of 2 drops of pico size carbon particles suspended in tall oil, then subjected to stirring. This second formulation is also referred to herein as CBD formulation according to the invention.

Example 2—Animal experiments and plasma collection: Male Wistar rats used in the study were, obtained from Sainath agencies, Hyderabad, India. The Animals were housed in the animal house facility of the University of Hyderabad. Animal experiments were carried out as per the approval from the Intuitional Animal Ethics Committee, University of Hyderabad. Adult male Wistar rats were maintained at 22° C. on 12-hour light and dark cycle in polyethylene cages with stainless steel lids with ad libitum access to food and water. Rats were kept for overnight fasting (12 hours). 10 mg/kg of CBD oil and CBD formulation according to the invention were administered orally to the rats using a cannula. The rats were euthanized at 0.5, 1, 2, 8, and 24 hours, and blood was collected by heart puncture into EDTA tubes. Plasma samples were obtained by centrifuging (1200 rpm, 15 minutes), at 4° C., and kept at −80° C. until analysis.

Example 3—BD estimation from plasma: 300 μl of plasma was aliquoted in an Eppendorf tube™ and 600 μl of acetonitrile was added thereto. The mixture was then kept for 5 minutes at −20° C. The collected sample was vortexed for 1 minute. After vortexing, 600 μl of distilled water was added and again vortexed for 1 minute. Then, 3 ml of n-hexane was added, then vortexed for 5 minutes. The sample was centrifuged at 1160×g for 15 minutes at 10° C. The organic layer was transferred to a tube and evaporated to dryness under a nitrogen environment at 35° C. The dried sample was solubilized in 500 μl acetonitrile. The amount of CBD from the sample was quantified using HPLC (Waters). The drug was resolved using C-18 column. The mobile phases used were acetonitrile and milli Q water (80:20 v/v). The flow rate was kept at 1 ml/min with an injection volume of 10 μl and a run time of 10 minutes. The absorption of CBD was kept at 220 nm. The concentrations estimated in 300 μl of plasma was computed to per ml concentration by multiplying with 3.33.

Example 4—Preparation of Calibration curve of Standard: The standard stock of 4 mg/ml of CBD was prepared by mixing with methanol. Serial dilutions 5, 10, 20, 40, 80 μg/ml of stock solution were prepared. The prepared samples were estimated using the Waters HPLC system. The standard curve is plotted using the data of area under the curve (AUC) vs CBD concentration and a straight line is plotted in Microsoft Excel. The concentration of CBD extracted from plasma was further derived from the line of equation ($y=mx+c$).

Pharmacokinetic analysis: Maximum plasma concentration attained (Cmax), time to reach Cmax (Tmax), partial area under the curve (AUC), partial area under the moment curve (AUMC), half-life of elimination (T half), and mean residence time (MRT) were calculated using Kinetica software. The obtained pharmacokinetic parameters were expressed as the mean±standard error of the mean.

Quantification of CBD using HPLC analysis: Standard curve for CBD concentration at the range of 5-80 μg/ml was obtained. Straight line with intercept 9783.3 and slope of 23390, and their correlation coefficient was 0.9998 (FIG. 1). Maximum concentration of CBD attained in the plasma for CBD in sesame oil and the CBD formulation according to the invention were 683.40 μg/ml and 1355.70 μg/ml, at 8 hours and 2 hours, respectively.

Figure 2:
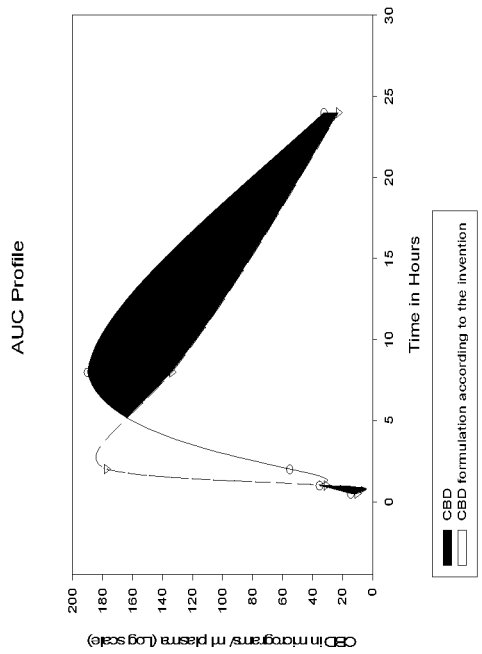
FIG. 2: AUC profile of CBD in sesame oil, and CBD in sesame oil mixed with pico size carbon particles suspended in tall oil (also referred to herein in as CBD formulation according to the invention or as formulation according to the invention); left panel is a line diagram, and right panel is a highlighted AUC.
Figure 2:
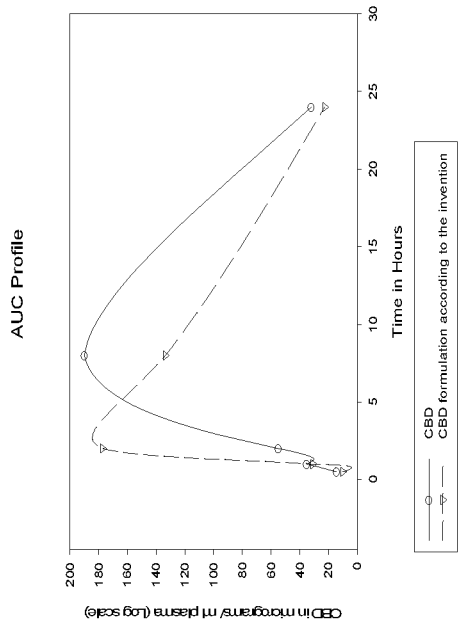

Bioavailability: Plasma is processed as explained in the method section, the CBD extracted from plasma was analyzed by HPLC and CBD concentrations were derived based on FIG. 1. When concentrations of CBD in plasma were plotted against time at which plasma was collected from the rat, the results in FIG. 2 show that oral administration of CBD, in the case of CBD in sesame oil, was slowly absorbed and reached maximum around 10 hours followed by slow elimination. When the CBD formulation according to the invention was administered orally, it was observed that an immediate intestinal absorption of the CBD reaching the peak and with significantly high within 4 hours. After reaching target peak, the concentration of CBD was observed to decrease in a biphasic manner, wherein there is an initial high rate of elimination from plasma, followed by a decrease in rate of elimination of CBD from plasma.

A similar profile has been reported using CBD dissolved in medium chain triglycerides in healthy men [7]. Further, 1.74-fold increase was observed in mean residence time for the CBD formulation according to the invention against CBD alone which was similar for CBD+nano formulation against CBD+oil alone where the increase in MRT fold was 1.39 [1]. In a study using CBD nano formulation, a 3.33-fold increase of CBD compared to CBD+oil alone was reported [1]. A single oral dose of the CBD formulation according to the invention resulted in a 1.34-fold increase in Cmax compared to CBD alone dissolved in sesame oil which was similar (1.18-fold increase) in comparison to CBD when delivered via nano emulsion in comparison to when it was delivered only with CBD and olive oil [1]. The Tmax of the CBD formulation according to the invention is found to be 4 hours. Medium-chain triglycerides-cannabidiol studied in men reported a Tmax of 4 hours [7].

TABLE 1

Pharmacokinetic parameters of CBD in sesame oil and the CBD formulation according to the invention, obtained using Kinetica software

| PK Parameter | | CBD | | CBD formulation according to the invention | |
| --- | --- | --- | --- | --- | --- |
| Parameter | Units | Mean | SD | Mean | SD |
| Cmax | µg/ml | 341.6638833 | 290.6545619 | 471.6940333 | 498.5924788 |
| Tmax | Hr | 10.66666667 | 5.96284794 | 4 | 3.098386677 |
| AUC | (hr)*(µg/ml) | 3314.326667 | 2229.779695 | 2773.001667 | 1686.953125 |
| AUMC | (hr)^2*(µg/ml) | 33618.7 | 20206.69253 | 23215.46667 | 14572.11556 |
| thalf | Hr | NA | NA | 12.6619025 | 7.865635467 |
| MRT | Hr | 11.02589 | 1.487806104 | 19.2615875 | 12.35457245 |

Nakno et al. [1] showed similar rapid absorption of CBD when nano emulsion of CBD is administered orally in rat though the plasma elimination is slow.

Also, it was noted that the rate of elimination is lower than the rate of absorption, which suggests that CBD retained well in the plasma. When comparing the results obtained with CBD in sesame oil and the CBD according to the invention, the rate of absorption and elimination is higher when with the CBD formulation according to the invention, while a similar bioavailability is observed in the two cases. This suggests that there is probably no inter cycle CBD accumulation in the plasma between the doses. In pharmacological application point of view the CBD formulation according to the invention would promote rapid absorption of CBD for triggering therapeutic activity of CBD quickly followed by slow elimination, which helps in reducing dose-related non-target effects.

Pharmacokinetic (PK) analysis: The plasma concentrations of CBD estimated in both formulations at different time points were computed for pharmacokinetic parameters using Kinetica 5.0 software. The results are presented in terms of mean±standard deviation in Table 1 below. When PK parameters obtained with the CBD formulation according to the invention and CBD in sesame oil are compared, the results show 1.34 times increase in Cmax, 2.66 times decrease in Tmax, 1.19 times decrease in AUC, 1.42 times decrease in AUMC, 1.746 times increase in MRT with the CBD formulation according to the invention.

Tmax obtained with the CBD formulation according to the invention was significantly lower than that obtained with CBD in sesame oil (4 vs. 10.66 hours) indicating an enhanced intestinal absorption of CBD when the CBD formulation according to the invention is used. It was reported in the art that CBD+nano formulation takes 8 hours compared to CBD+oil alone (2 hours) [1]. In our study, a As will be understood by a skilled person, CBD exhibits poor absorption when given orally due its poor solubility in water and ample first-pass metabolism. The present invention provides a novel CBD formulation which is relatively simple to prepare. An oil-based material consisting of pico size carbon particles suspended in tall oil is added to CBD dissolved in sesame oil, and the mixture is subjected to stirring, leading to the CBD formulation according to the invention. The results show that the CBD formulation according to the invention promotes a rapid intestinal absorption of CBD through oral route. Moreover, the results show an improved pharmacokinetic profile in terms of better absorption, increase in Cmax, and slower elimination rate of CBD. Accordingly, the CBD formulation according to the invention may be used as a quick therapeutic active formulation in acute conditions approved for treatment using CBD in oral route.

As will be understood by a skilled person, CBD may be dissolved in any other suitable oil-based material than sesame oil, such as for example tall oil, hydrocarbon, higher fatty acid, higher alcohol, fatty acid ester of polyhydric alcohol, higher alcohol ether of polyhydric alcohol, polymer or copolymer of alkylene oxide, long chain triglycerides (LCT), medium chain triglycerides (MCT), and a combination thereof.

As will be understood by a skilled person, the pico size carbon particles may be suspended in any other suitable oil-based material that tall oil, such as for example sesame oil, hydrocarbon, higher fatty acid, higher alcohol, fatty acid ester of polyhydric alcohol, higher alcohol ether of polyhydric alcohol, polymer or copolymer of alkylene oxide, long chain triglycerides (LCT), medium chain triglycerides (MCT), and a combination thereof.

As will be understood by a skilled person, the oil-based material in which CBD is dissolved and the oil-based material in which the pico size carbon particles are suspended may be the same or they may be different. Also, each oil-based material may independently be a mixture of two or more oil-based materials.

As will be understood by a killed person, the relative amounts of CBD and pico size carbon particles may vary depending for example on the intended use of the formulation. Incidentally, the relative amount of the CBD dissolved in an oil-based material and the oil-based suspension of pico size carbon particles may vary depending for example on the intended use of the formulation.

As will be understood by a skilled person, during the production method, after addition of the oil-based suspension of pico size carbon particles to the CBD dissolved in an oil-based material, the time period for subjecting the resulting mixture to stirring may vary depending for example on the amount of the formulation according to the invention being produced.

As will be understood by a skilled person, the CBD formulation according to the invention may further comprise other suitable ingredients including for example a flavor agent which is artificial or from a natural source, a coloring agent which is artificial or from a natural source, caffeine, an antioxidant, a vitamin, a probiotic, a mineral, and a combination thereof.

The oil-based formulation according to the invention may be used for treating a patient in need of a cannabinoid. In embodiments of the invention, the patient may have a medical condition which is epilepsy such as childhood-onset epilepsy which may be Lennox-Gastaut syndrome or Dravet syndrome. In embodiments of the invention, administration of the formulation to the patient is an oral administration. Seizure frequency in the patient may be reduced following administration of the formulation. In embodiments of the invention, the medical condition is resistant from other treatments including a treatment involving clobazam.

The scope of the claims should not be limited by the preferred embodiments set forth in the examples; but should be given the broadest interpretation consistent with the description as a whole.

The present description refers to a number of documents, the content of which is herein incorporated by reference in their entirety.

REFERENCES

1. Yukako Nakano et al., Development of a Novel Nanoemulsion Formulation to Improve Intestinal Absorption of Cannabidiol, *Med. Cannabis Cannabinoids* (2019) 2:35-42.
2. World Health Organization Expert Committee on Drug Dependence: Cannabidiol (CBD) Pre-Review Report Agenda Item 5.2 and Peer Review, 2017. Available at: https://www.who.int/medicines/access/controlled-substances/5.2_CBD.pdf.
3. Jacob Atsmon, Daphna Heffetz, Lisa Deutsch, Frederic Deutsch, and Hagit Sacks, Single-Dose Pharmacokinetics of Oral Cannabidiol Following Administration of PTL101: A New Formulation Based on Gelatin Matrix Pellets Technology, *Clinical Pharmacology in Drug Development* (2018) September; 7(7):751-758.
4. Christian Larsena, Jorida Shahinas, Dosage, Efficacy and Safety of Cannabidiol Administration in Adults: A Systematic Review of Human Trials, *J. Clin. Med. Res.* (2020) 12(3):129-141.
5. A Thomas, G L Baillie, A M Phillips, R K Razdan, R A Ross, R G Pertwee, Cannabidiol displays unexpectedly high potency as an antagonist of CB1 and CB2 receptor agonists in vitro, *Br. J. Pharmacol.* (2007) 150(5):613-23.
6. Timothy E. Welty, Adrienne Luebke, Barry E. Gidal, Cannabidiol: Promise and Pitfalls, Epilepsy Currents. 2014; 14(5): 250-252.
7. Katharina Knaub, Tina Sartorius, Tanita Dharsono, Roland Wacker, Manfred Wilhelm, Christiane Schön, A Novel Self-Emulsifying Drug Delivery System (SEDDS) Based on VESIsorbfi Formulation Technology Improving the Oral Bioavailability of Cannabidiol in Healthy Subjects, *Molecules* (2019) 24, 2967.
8. Millar S. A. et al. Towards Better Delivery of Cannabidiol (CBD), *Pharmaceuticals* (2020) 13, 219.

The invention claimed is:

1. An oil-based formulation comprising a cannabinoid dissolved in a first oil-based material and pico size carbon particles suspended in a second oil-based material, wherein the first oil-based material is sesame oil and the second oil-based material is tall oil.

2. The oil-based formulation according to claim 1, wherein the cannabinoid is purified from a cannabis extract or the cannabinoid is synthesized.

3. The oil-based formulation according to claim 1, wherein the cannabinoid is a cannabis extract enriched in cannabidiol (CBD).

4. The oil-based formulation according to claim 1, wherein the cannabinoid comprises cannabidiol (CBD) and one or more of: tetrahydrocannabinol (Δ9-THC), cannabichromene (CBC), cannabigerol (CBG), cannabinol (CBN), cannabidivarol (CBDV), and a salt of the cannabinoid.

5. The oil-based formulation according to claim 1, wherein the cannabinoid is cannabidiol (CBD).

6. The oil-based formulation according to claim 1, further comprising one or more of: a flavor agent which is artificial or from a natural source, a coloring agent which is artificial or from a natural source, caffeine, an antioxidant, a vitamin, a probiotic, and a mineral.

7. The oil-based formulation according to claim 1, which is suitable for medical administration to a patient in need of cannabinoid.

8. A method of treating a patient in need of a cannabinoid, comprising administering to the patient a suitable amount of the oil-based formulation as defined in claim 1.

9. A pharmaceutical composition comprising the oil-based formulation as defined in claim 1, and a pharmaceutically acceptable carrier or excipient.

10. A method for producing a formulation comprising a cannabinoid, the method comprising:
    (a) dissolving a cannabinoid in a first oil-based material which is sesame oil to obtain a first mixture;
    (b) providing a suspension of pico size carbon particles in a second oil-based material which is tall oil; and
    (c) adding the suspension to the first mixture and stirring the resulting mixture for a period of time to obtain the formulation.

11. The method according to claim 10, wherein the cannabinoid is cannabidiol (CBD).

12. A kit comprising:
    a cannabinoid;
    an oil-based material which is sesame oil;
    a suspension of pico size carbon particles in a second oil-based material which is tall oil; and
    instructions for use,
    optionally, the use is for the preparation of a medicament for treating a patient in need of a cannabinoid.

13. The kit according to claim 12, wherein the cannabinoid is cannabidiol (CBD).

14. The method according to claim 8, wherein the patient has a medical condition which is epilepsy; optionally the medical condition is childhood-onset epilepsy selected from Lennox-Gastaut syndrome and Dravet syndrome; optionally administration to the patient is an oral administration; optionally seizure frequency in the patient is reduced; optionally the medical condition is resistant from other treatments including a treatment involving clobazam.

15. The method according to claim 8, wherein the cannabinoid is cannabidiol (CBD).

* * * * *